United States Patent [19]

Yagihara et al.

[11] 4,157,916

[45] Jun. 12, 1979

[54] SILVER HALIDE PHOTOGRAPHIC LIGHT-SENSITIVE MATERIAL

[75] Inventors: Morio Yagihara; Mitsugu Tanaka; Toshiaki Aono; Takeshi Hirose, all of Minami-ashigara, Japan

[73] Assignee: Fuji Photo Film Co., Ltd., Minami-ashigara, Japan

[21] Appl. No.: 815,407

[22] Filed: Jul. 13, 1977

[30] Foreign Application Priority Data

Jul. 13, 1976 [JP] Japan .................................. 51-83363

[51] Int. Cl.² .................. G03C 7/00; G03C 5/30; G03C 1/76
[52] U.S. Cl. .................................... 96/56.5; 96/66.3; 96/74; 96/95; 96/100 R
[58] Field of Search ............... 96/100, 55, 56.5, 66.3, 96/74, 95

[56] References Cited

U.S. PATENT DOCUMENTS

| | | | |
|---|---|---|---|
| 2,269,481 | 1/1942 | Reindorp | 96/100 |
| 3,933,500 | 1/1976 | Shiba et al. | 96/56.5 |
| 3,984,245 | 10/1976 | Hirose et al. | 96/100 |
| 3,990,899 | 11/1976 | Shiba et al. | 96/74 |

*Primary Examiner*—J. Travis Brown
*Attorney, Agent, or Firm*—Sughrue, Rothwell, Mion, Zinn and Macpeak

[57] ABSTRACT

A silver halide photographic light-sensitive material containing a novel development inhibitor releasing coupler compound, capable of forming a substantially colorless product, represented by the following general formula (I):

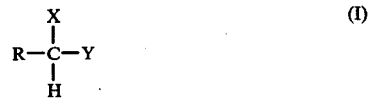

wherein R represents

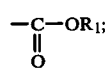

X represents

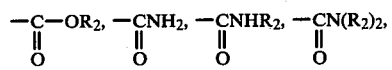

$-SO_2R_2$, $-SO_2OR_2$, $-SO_2N(R_2)_2$, $-SO_2NHR_2$, $-CN$, $-N^+(R_2)_3$ or

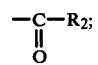

$R_1$ and $R_2$ each represents an aliphatic group, an aromatic group or a heterocyclic group and further two $R_2$ groups can combine and represent an atomic group necessary to form, together with the nitrogen atom to which they are attached, a nitrogen-containing heterocyclic group; and Y represents a group capable of being released from the compound represented by the general formula (I) upon reaction with the oxidation product of a color developing agent to provide a compound which has a development inhibiting effect and having a triazole ring bonded to the carbon atom through the nitrogen atom at the 1-position thereof.

16 Claims, 2 Drawing Figures

- PC : PROTECTIVE LAYER
- BL : BLUE-SENSITIVE EMULSION LAYER
- YF : YELLOW FILTER LAYER
- GL : GREEN-SENSITIVE EMULSION LAYER
- ML1 : INTERMEDIATE LAYER
- RL : RED-SENSITIVE EMULSION LAYER
- ML2 : INTERMEDIATE LAYER
- AHL : ANTIHALATION LAYER
- SUPPORT $\Delta D^G = D_1^G - D_2^G$

SILVER HALIDE PHOTOGRAPHIC LIGHT-SENSITIVE MATERIAL

BACKGROUND OF THE INVENTION

1. FIELD OF THE INVENTION

The present invention relates to a silver halide photographic light-sensitive material containing a novel compound capable of releasing a development inhibitor.

2. DESCRIPTION OF THE PRIOR ART

It is known that a compound which provides a development inhibitor in an amount depending on the optical density of an image formed upon development can be used by addition to a photographic light-sensitive material. Such a compound generally releases a development inhibitor by reaction with the oxidation product of a color developing agent. Typical development inhibitor releasing (DIR) compounds of this type include the so-called DIR couplers, the active site of which contains a group which exhibits a development inhibiting action when it is split from the active site. DIR couplers form dyes by coupling with the oxidation product of a color developing agent and release development inhibitors. Compounds such as those disclosed in U.S. Pat. Nos. 3,227,554, 3,701,783, 3,615,506, 3,617,291 and the like are known DIR couplers.

DIR couplers are employed for the purpose of controlling the image tone, reducing graininess of the image, improving sharpness of the image due to edge effects, improving color reproduction due to interlayer effects, and the like as is well known from the disclosure in the above-mentioned patent specifications.

However, in many cases, DIR couplers as described in U.S. Pat. No. 3,227,554, etc., do not exert the desired inhibiting effect resulting in a degradation of the photographic properties and storage properties because the dye yield upon development adversely affects color reproduction unless the proper type of coupler residue and the proper amount of coupler are precisely chosen, and a convenient selection of a coupler residue for color reproduction restricts the permissible reactivity of the oxidation product of the color developing agent and the coupler. In addition, DIR couplers of this type have various disadvantages such as poor stability against ageing, they often exhibit a desensitization effect, they produce mottle resulting from contamination of the developer solution and the like.

The so-called non-color forming type of coupling compounds were developed with the intention of eliminating these disadvantages, which coupling compounds form essentially colorless products or colored products, whose color, however, change and become essentially colorless in the course of photographic treatment upon undergoing a coupling reaction with the oxidation product of a color developing agent, and also yield a development inhibitor at the same time. Known compounds of this type are disclosed in U.S. Pat. Nos. 3,632,345, 3,928,041, 3,958,993 and 3,961,959 and the like. While these compounds have advantageous properties, they also have some drawbacks. For example, the stain resulting from the products formed by the reaction of these compounds and the oxidation products of color developing agents is one drawback of the compounds. Their most serious drawback, however, is the low reactivity of the coupling compounds with the oxidation products of color developing agents. Accordingly, a large amount of these compounds must be employed because of their low reactivity and this results in a decrease in the photographic properties and a reduction in shelf life. Further, all of the compounds disclosed in the above-described U.S. patent specifications yield mercapto group-containing compounds by reacting with the oxidation product of a developing agent. When compounds of this type are employed for producing multilayer color photographs, the resulting development inhibiting agent tends to remain in the layer in which the compound was incorporated, i.e., it diffuses only with difficulty into other layers. Therefore, these compounds contribute only slightly to the so-called interlayer effect, resulting in unsatisfactory color correction, and resistance to desilvering in the bleaching step tends to occur. In order to improve these drawbacks, the compounds as described in U.S. Pat. No. 3,933,500 are known. While the photographic properties are improved to a certain extent, it is desirable to provide a DIR coupler which has further improved properties in that the DIR coupler has an extremely high reactivity with the oxidation product of a color developing agent so as to yield sufficient image improving effects with the use of a small amount thereof, and in that the color of the compound which is formed by the reaction of the DIR coupler with the oxidation product of a color developing agent does not substantially affect the finished color image when the DIR compound is used in a light-sensitive material.

SUMMARY OF THE INVENTION

Therefore, a first object of the present invention is to provide a novel DIR coupler.

A second object of the present invention is to provide a DIR coupler which rapidly reacts with the oxidation product of a developing agent to result in the release of a compound with a development inhibiting action.

A third object of the present invention is to provide a DIR coupler which provides sufficient control of the image tone, sufficiently reduced graininess of the image, sufficiently improved sharpness of the image and sufficiently improved color reproduction.

A fourth object of the present invention is to provide a novel DIR coupler which yields, upon reaction with the oxidation product of a color developing agent, a color which does not contribute substantially to the finished color image.

A fifth object of the present invention is to provide a silver halide photographic light-sensitive material containing a novel DIR coupler.

A sixth object of the present invention is to provide a photographic processing solution containing a novel DIR coupler.

A seventh object of the present invention is to provide a method for forming an image wherein the processing is carried out in the presence of a novel DIR coupler.

These objects of the present invention are attained with a DIR coupler which, upon reaction with the oxidation product of a color developing agent, releases a development inhibitor and which is represented by the following general formula (I):

(I)

wherein R represents

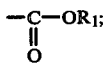

X represents

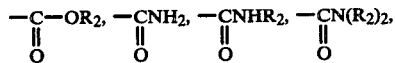

—SO$_2$R$_2$, —SO$_2$OR$_2$, —SO$_2$N(R$_2$)$_2$, —SO$_2$NHR$_2$, —CN, —N$^+$(R$_2$)$_3$ or

R$_1$ and R$_2$ each represents an aliphatic group, an aromatic group or a heterocyclic group, and two R$_2$ groups may combine and represent an atomic group necessary to form, together with the nitrogen atom to which they are attached, a nitrogen-containing heterocyclic group.

Accordingly, this invention provides a photographic silver halide emulsion containing a coupling compound represented by the following general formula (I):

$$R-\underset{\underset{H}{|}}{\overset{\overset{X}{|}}{C}}-Y \quad (I)$$

wherein R represents

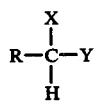

X represents

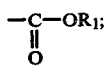

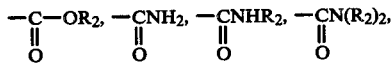

—SO$_2$R$_2$, —SO$_2$OR$_2$, —SO$_2$N(R$_2$)$_2$, —SO$_2$NHR$_2$, —CN, —N$^+$(R$_2$)$_3$ or

R$_1$ and R$_2$ each represents an aliphatic group, an aromatic group or a heterocyclic group and further two R$_2$ groups can combine and represent an atomic group necessary to form, together with the nitrogen atom to which they are attached, a nitrogen-containing heterocyclic group; and Y represents a group capable of being released from the compound represented by the general formula (I) upon reaction with the oxidation product of a color developing agent to provide a compound which has a development inhibiting effect and having a triazole ring bonded to the carbon atom through the nitrogen atom at the 1-position thereof.

Further, an embodiment of this invention comprises a photographic light-sensitive material comprising a support having thereon at least one layer of the silver halide emulsion containing the coupling compound represented by the general formula (I) above, a photographic developer solution containing a coupling compound represented by the general formula (I) above and a method for forming a photographic image comprising developing an imagewise exposed photographic light-sensitive material having thereon at least one silver halide emulsion layer in the presence of a coupling compound represented by the general formula (I) above.

BRIEF DESCRIPTION OF THE ACCOMPANYING DRAWINGS

FIG. 1 shows a cross sectional view of the layer structure of Samples 301 to 305 prepared as described in Example 3.

FIG. 2 indicates the definition of $\Delta D^G$ which means the amount of interlayer effects obtained by exposure in the manner as described in Example 3.

DETAILED DESCRIPTION OF THE INVENTION

Figure 1:
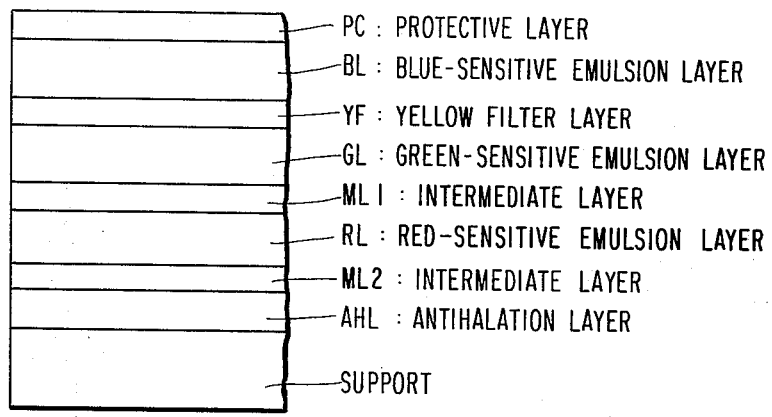

The aliphatic group represented by R$_1$ or R$_2$ is preferably an aliphatic group having 1 to 25 carbon atoms which can be saturated or unsaturated, straight chain, branched chain or cyclic and be substituted with one or more substituents, for example, an alkoxy group (such as a methoxy group, an isopropoxy group, etc.), a halogen atom (such as a chlorine atom, a bromine atom, etc.), a hydroxy group, a carboxy group, a sulfo group, a heterocyclic group (such as a tetrahydrofuran group, a pyridine group, etc.), an aryl group (such as a phenyl group, a tolyl group, etc.), an aralkyl group (such as a benzyl group, a phenethyl group, a styryl group, etc.), and the like.

The aromatic group represented by R$_1$ to R$_2$ is preferably an aryl group having 6 to 35 total carbon atoms and includes an unsubstituted phenyl group or a phenyl group substituted with one or more substituents. Suitable substituents include monovalent substituents, for example, a halogen atom (such as a fluorine atom, a chlorine atom, a bromine atom, etc.), a nitro group, a cyano group, a thiocyano group, a hydroxy group, an alkoxy group (preferably an alkoxy group having 1 to 20 carbon atoms, such as a methoxy group, an isopropoxy group, an octoxy group, etc.), an aryloxy group (such as a phenoxy group, a nitrophenoxy group, etc.), an alkyl group (preferably an alkyl group having 1 to 20 carbon atoms, such as a methyl group, an ethyl group, a dodecyl group, etc.), an alkenyl group (preferably an alkenyl group having 1 to 20 carbon atoms, such as an allyl group, etc.), an aryl group (preferably an aryl group having 6 to 10 carbon atoms, such as a phenyl group, a tolyl group, etc.), an amino group (for example, an unsubstituted amino group, an alkylamino group having 1 to 20 carbon atoms, such as a diethylamino group, an octylamino group, etc.), a carboxy group, an acyl group (preferably an acyl group having 2 to 20 carbon atoms, such as an acetyl group, a decanoyl group, etc.), an alkoxycarbonyl group (preferably an alkoxycarbonyl group having 1 to 20 carbon atoms in the alkyl moiety, such as a methoxycarbonyl group, a butoxycarbonyl group, an octoxycarbonyl group, a dodecyloxycarbonyl group, a 2-phenylethoxycarbonyl group, a 2-methoxyethoxycarbonyl group, etc.), an aryloxycarbonyl group (preferably an aryloxycarbonyl group having 6 to 20 carbon atoms in the aryl moiety, such as a phenoxycarbonyl group, a tolyloxycarbonyl group, etc.), a carbamoyl group (for example, an ethylcarbamoyl group, an octylcarbamoyl group, etc.), an acylamino group (preferably an acylamino group having 2 to 21 carbon atoms, such as an acetamido group, an octanamido group, 2 2,4-di-tert-pentylphenoxyacetamido group, etc.), a sulfo group, an alkylsulfonyl group (preferably an alkylsulfonyl group having 1 to 20 carbon atoms, such as a methylsulfonyl group, an octylsulfonyl group, etc.), an arylsulfonyl group (preferably an arylsulfonyl group having 6 to 20 carbon atoms, such as a phenylsulfonyl group, a naphthylsulfonyl group, etc.), an alkoxysulfonyl group (preferably an alkoxysulfonyl group having 1 to 20 carbon atoms, such as a methoxysulfonyl group, an octoxysulfonyl group, etc.), an aryloxysulfonyl group (preferably an aryloxysulfonyl group having 6 to 20 carbon atoms, such as a phenoxysulfonyl group, etc.), a sulfamoyl group (preferably a sulfamoyl group having 1 to 20 carbon atoms, such as a diethylsulfamoyl group, an octylsulfamoyl group, a methyloctadecylsulfamoyl group, etc.), a sulfonamido group (preferably a sulfonamido group having 1 to 20 carbon atoms, such as a methylsulfonamido group, an octylsulfonamido group, etc.) and the like, or a divalent substituent which forms a condensed ring with the phenyl group (for example, a divalent group forming a naphthalene ring, etc.).

The heterocyclic group represented by $R_1$ or $R_2$ includes a 5-membered or 6-membered heterocyclic group (for example, a 5-membered or 6-membered heterocyclic group containing at least one hetero atom such as a nitrogen atom, an oxygen atom, a sulfur atom, etc., e.g., 1 to 4 nitrogen atoms, 1 to 2 oxygen atoms and/or 1 sulfur atom, which group may have one or more fused benzene rings or naphthalene rings. When two or more $R_2$ groups are present, each $R_2$ can be the same or different. Further, two $R_2$ groups in, for example, the $-N^+(R_2)_3$ group, the $-SO_2N(R_2)_2$ group or the like can combine and form a saturated 5-membered or 6-membered heterocyclic ring together with the nitrogen atom to which they are attached (for example, a piperidine ring, a pyrrolidine ring, a morpholine ring, etc.). $R_1$ and $R_2$ can be the same or different.

Y represents a group capable of being released from the compound represented by the general formula (I) upon reaction with the oxidation product of a developing agent to provide a compound which has a development inhibiting effect and having a triazole ring bonded to the carbon atoms of the coupler skeleton through the nitrogen atom at the 1-position thereof and the triazole ring can be part of a condensed ring system or can contain one or more substituents. Of the triazole rings represented by Y, a benzotriazolyl group, a naphthotriazolyl group and a triazolyl group are preferred. These groups can have one or more substituents. Suitable substituents include a halogen atom (such as a fluorine atom, a chlorine atom, a bromine atom, etc.), an acyl group (preferably an acyl group having 2 to 20 carbon atoms, such as an acetyl group, a decanoyl group, etc.), an alkoxycarbonyl group (preferably an alkoxycarbonyl group having 1 to 20 carbon atoms in the alkyl moiety, such as a methoxycarbonyl group, a butoxycarbonyl group, an octoxycarbonyl group, a dodecyloxycarbonyl group, a 2-phenylethoxycarbonyl group, a 2-methoxyethoxycarbonyl group, etc.), a hydroxy group, a carboxy group, a nitro group, a cyano group, an aryl group (preferably an aryl group having 6 to 35 carbon atoms, such as a phenyl group, a naphthyl group, a tolyl group, etc.), an alkoxy group (preferably an alkoxy group having 1 to 20 carbon atoms, such as a methoxy group, an isopropoxy group, an octoxy group, etc.), an aryloxy group (such as a phenoxy group, a chlorophenoxy group, a nitrophenoxy group, etc.), an acylamino group (preferably an acylamino group having 2 to 21 carbon atoms, such as an acetamido group, an octanamido group, a 2,4-di-tert-pentylphenoxyacetamido group, etc.), a sulfo group, an amino group (for example, an unsubstituted amino group, an alkylamino group having 1 to 20 carbon atoms, such as a diethylamino group, an octylamino group, etc.), an alkyl group (preferably an alkyl group having 1 to 20 carbon atoms, such as a methyl group, an ethyl group, a dodecyl group, etc.), an alkenyl group (preferably an alkenyl group having 1 to 20 carbon atoms, such as an allyl group, etc.), a sulfamoyl group (preferably a sulfamoyl group having 1 to 20 carbon atoms, such as a diethylsulfamoyl group, an octylsulfamoyl group, a methyloctadecylsulfamoyl group, etc.), a sulfonamido group (preferably a sulfonamido group having 1 to 20 carbon atoms, such as a methanesulfonamido group, a toluenesulfonamido group, a hexadecanesulfonamido group, etc.), a carbamoyl group (preferably a carbamoyl group having 1 to 20 carbon atoms, such as an ethylcarbamoyl group, an octylcarbamoyl group, etc.), a ureido group (for example, an alkylureido group, an arylureido group, a heterocyclic ureido group, etc.), an alkoxycarbonylamino group, an alkylthio group (preferably an alkylthio group having 1 to 20 carbon atoms, such as a methylthio group, a butylthio group, a hexadecylthio group, etc.), an alicyclic hydrocarbon group (such as a cyclohexyl group, a cyclopentyl group, a cyclopropyl group, etc.), a thiocyano group, an aryloxycarbonyl group (preferably an aryloxycarbonyl group having 6 to 20 carbon atoms in the aryl moiety, such as a phenoxycarbonyl group, a tolyloxycarbonyl group, etc.), an alkylsulfonyl group (preferably an alkylsulfonyl group having 1 to 20 carbon atoms, such as a methylsulfonyl group, an octylsulfonyl group, etc.), an arylsulfonyl group (preferably an arylsulfonyl group having 6 to 20 carbon atoms, such as a phenylsulfonyl group, a naphthylsulfonyl group, etc.), an alkoxysulfonyl group (preferably an alkoxysulfonyl group having 1 to 20 carbon atoms, such as a methoxysulfonyl group, an octoxysulfonyl group, etc.), an aryloxysulfonyl group (preferably an aryloxysulfonyl group having 6 to 20 carbon atoms, such as a phenoxysulfonyl group, etc.), a heterocyclic group (such as a 4-thiaxolin-5-thione group, a pyridyl group, etc.), an aralkyl group (preferably an aralkyl group having 7 to 30 carbon atoms, such as a benzyl group, a phenylethyl group, etc.), an aralkoxy group (preferably an aralkoxy group having 7 to 30 carbon atoms, such as a benzyloxy group, a phenethyloxy group, etc.), an imino group, and a group represented by the general formula (II) or (III):

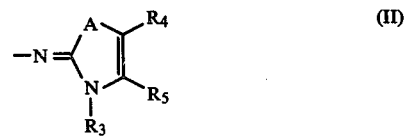

wherein A represents a sulfur atom, a selenium atom or an oxygen atom; $R_3$ represents an aliphatic group (e.g., an aliphatic group having 1 to 15 carbon atoms, such as an ethyl group, an n-octyl group, an isopropyl group, etc.), and $R_4$ and $R_5$ each represents a hydrogen atom, an aliphatic group (e.g., an aliphatic group having 1 to 15 carbon atoms, such as an ethyl group, an n-octyl group, an isopropyl group, etc.), an alkoxy group or a hydroxy group and $R_4$ and $R_5$ can combine and represent an atomic group necessary to form a benzene ring or a naphthalene ring.

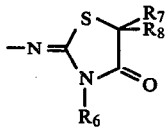

wherein $R_6$ represents an aliphatic group (e.g., as described above for $R_3$); and $R_7$ and $R_8$, which may be the same or different, each represents a hydrogen atom or an aliphatic group (e.g., as described above for $R_4$ and $R_5$). When two or more substituents are present, these can be the same or different.

Preferred examples of groups represented by X in the above-described general formula (I) are

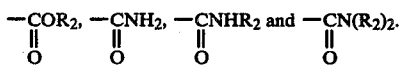

In the general formula (I), the compound having

for R and

for X wherein $R_1$ and $R_2$ each represents an aliphatic group, an aromatic group or a heterocyclic group and each of these groups is the same as defined above and $R_1$ and $R_2$ may be the same or different is particularly preferred.

Of the groups represented by Y, a benzotriazolyl group is particularly preferred and the group can have one or more substituents, which may be the same or different. Suitable substituents include, for example, a halogen atom, an acyl group, an alkoxycarbonyl group, a carboxy group, a sulfo group, a nitro group, an acylamino group, a ureido group, a carbamoyl group, a sulfamoyl group, an alkoxy group, an aryloxy group, an alkyl group, a heterocyclic group, an aralkyloxy group, an aryl group, an amino group, an imino group, a group represented by the above-described general formula (II) or (III), etc. Specific examples of suitable substituents are the same as those described above for Y in the general formula (I) described above.

Of the substituents represented by the general formula (II), a group represented by the following general formula (IIA)

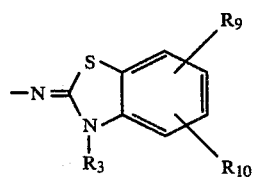

wherein $R_3$ represents an aliphatic group; and $R_9$ and $R_{10}$ each represents a hydrogen atom, a halogen atom, an aliphatic group, an alkoxy group, a hydroxy group or an aromatic group; is particularly preferred as a substituent for the benzotriazolyl group.

The aliphatic group represented by $R_3$ includes an unsubstituted alkyl group having 1 to 18 carbon atoms (such as a methyl group, an ethyl group, an n-propyl group, an isopropyl group, an n-butyl group, a tert-butyl group, a heptadecyl group, etc.), a substituted alkyl group having 1 to 4 carbon atoms in the alkyl moiety, for example, a sulfoalkyl group (such as a 2-sulfoethyl group, a 3-sulfopropyl group, a 3-sulfobutyl group, a 2-hydroxy-3-sulfopropyl group, a 4-sulfobutyl group, etc.), a carboxyalkyl group (such as a 2-carboxyethyl group, a 4-carboxybutyl group, a carboxymethyl group, etc.), a hydroxyalkyl group (such as a 2-hydroxyethyl group, a 3-hydroxypropyl group, etc.), an alkoxyalkyl group including a substituted alkoxyalkyl group (such as a 2-methoxyethyl group, a 3-methoxypropyl group, a 2-(2-sulfoethoxy)ethyl group, a 2-[2-(3-sulfopropoxy)ethoxy]ethyl group, a hydroxymethoxymethyl group, a 2-hydroxyethoxymethyl group, a 2-(2-hydroxyethoxy)ethyl group, a 2-(2-acetoxyethoxy)ethyl group, an acetoxymethoxymethyl group, etc.), an acyloxyalkyl group (such as a 2-acetoxyethyl group, a 4-propionyloxybutyl group, etc.), a dialkylaminoalkyl group (such as a dimethylaminoethyl group, a diethylaminopropyl group, etc.), a sulfatoalkyl group (such as a $\beta$-sulfatoethyl group, a 4-sulfatobutyl group, etc.), an aralkyl group (such as a benzyl group, a phenethyl group, a p-sulfobenzyl group, etc.), an alkenyl group (such as a vinylmethyl group, etc.), and the like.

$R_9$ and $R_{10}$, which may be the same or different, each represents a hydrogen atom, a halogen atom, an aliphatic group, an alkoxy group, a hydroxy group or an aromatic group.

Suitable halogen atoms each represented by $R_9$ and $R_{10}$ include, for example, a chlorine atom, a bromine atom, an iodine atom, etc.

The aliphatic group each represented by $R_9$ and $R_{10}$ includes an unsubstituted alkyl group having 1 to 18 carbon atoms (such as a methyl group, an ethyl group, an isopropyl group, an n-butyl group, a tert-butyl group, a heptadecyl group, etc.), a substituted alkyl group having 1 to 12 carbon atoms in the alkyl moiety, for example, a sulfoalkyl group (such as a 2-sulfoethyl group, a 3-sulfopropyl group, a 3-sulfobutyl group, a 4-sulfobutyl group, a 2-hydroxy-3-sulfopropyl group, etc.), a carboxyalkyl group (such as a 2-carboxyethyl group, a 4-carboxybutyl group, a carboxymethyl group, etc.), a hydroxyalkyl group (such as a $\beta$-hydroxyethyl group, a $\gamma$-hydroxypropyl group, etc.), an alkoxyalkyl group including a substituted alkoxyalkyl group (such as a $\beta$-methoxyethyl group, a $\gamma$-methoxypropyl group, a propargyloxymethyl group, a 2-propargyloxyethyl group, a 2-(2-sulfoethoxy)ethyl group, a 2-[2-(3-sulfopropoxy)ethoxy]ethyl group, a hydroxymethoxymethyl group, a 2-hydroxyethoxymethyl group, a 2-(2-hydroxyethoxy)ethyl group, a 2-(2-acetoxyethoxy)ethyl group, an acetoxymethoxymethyl group, etc.), an acyloxyalkyl group (such as a 2-acetoxyethyl group, a 4-propionyloxybutyl group, etc.), a dialkylaminoalkyl group (such as a dimethylaminoethyl group, a diethylaminopropyl group, etc.), a haloalkyl group (such as a trifluoromethyl group, etc.), a sulfatoalkyl group (such as a $\beta$-sulfatoethyl group, an $\omega$-sulfatobutyl group, etc.), an aralkyl group (such as a benzyl group, a phenethyl group, a p-sulfobenzyl group, etc.), an alkenyl group (such as a vinylmethyl group, etc.), and the like.

The aromatic group each represented by $R_9$ and $R_{10}$ includes a monocyclic or bicyclic aryl group, preferably a monocyclic aryl group, and can be an unsubstituted aryl group (such as a phenyl group, a naphthyl group, etc.), and a substituted aryl group, for example, a phenyl group having, as substituents, one or more of an alkyl group having 1 to 4 carbon atoms (such as a methyl group, etc.), an alkoxy group having 1 to 4 carbon atoms (such as a methoxy group, an ethoxy group, etc.), a hydroxy group, a halogen atom (such as a chlorine atom, etc.), a sulfo group and the like. Specific examples of substituted phenyl groups are a p-tolyl group, a p-methoxyphenyl group, a p-hydroxyphenyl group, a 2,4-dimethoxyphenyl group, a p-chlorophenyl group, a p-sulfophenyl group, etc.

Further, $R_9$ and $R_{10}$ each represents an alkoxy group having 1 to 18 carbon atoms, for example, an unsubstituted alkoxy group (such as a methoxy group, an ethoxy group, a propargyloxy group, etc.), or a substituted alkoxy group (such as a benzyloxy group, an α-naphthylmethyloxy group, etc.).

$R_9$ and $R_{10}$, preferably, each represents a hydrogen atom, a methyl group, an ethyl group, a chlorine atom, a methoxy group, an ethoxy group or a hydroxy group.

Representative examples of benzotriazole type releasable groups are, for example, a 5- or 6-benzyloxybenzotriazol-1-yl group, a 5- or 6-octanamidobenzotriazol-1-yl group, a 5- or 6-(3-methylbenzothiazolinyliden)aminobenzotriazol-1-yl group, a 5- or 6-(3-ethylbenzothiazolinyliden)aminobenzotriazol-1-yl group, a 5- or 6-(3-benzylbenzothiazolinyliden)aminobenzotriazol-1-yl group, and the like.

The DIR coupler according to the present invention has remarkably superior properties in comparison with known DIR couplers in that it has a high coupling activity and extremely high development inhibiting effect, reduced graininess and improved sharpness, in that the compound per se is stable and thus the light-sensitive materials containing the compound have improved ageing properties, and further in that when the DIR coupler of the present invention is used in a light-sensitive material, the color formed by the reaction of the DIR coupler with the oxidation product of a color developing agent hardly makes any contribution to color images. It can, therefore, be used without concern in a layer such as a green-sensitive layer or a red-sensitive layer containing a coupler which forms a dye having a color different from that of the dye formed from the compound of the present invention. That is, the coupler of the present invention can be used simultaneously in each of three layers in a color photographic film, which is extremely advantageous from the viewpoint of cost and emulsion design. Furthermore, using the DIR coupler of the present invention, improvements in graininess, particularly in the low density areas, and large interlayer color correction effects are achieved.

Moreover, the silver removal property in the bleaching step is not deteriorated in case of using the coupler of the present invention.

DIR couplers having a 2-benzotriazolyl group which emit strong fluorescence are described in Japanese Patent Publication 8750/1972. However, the DIR coupler used in the present invention does not have this fluorescence emission property which is undesirable in practical use in case the compounds as described in Japanese Patent Application (OPI) 122,335/1974 (corresponding to U.S. Pat. No. 3,933,500), since the triazole ring thereof is bonded through the nitrogen atom at the 1-position to the carbon atom of the coupling position. Thus, the coupler of the present invention also has various advantages as described in page 173 of Japanese Patent Application (OPI) 122,335/1974. For reference, where the triazole ring is bonded through the nitrogen atom at the 1-position and where the triazole ring is bonded through the nitrogen atom at the 2-position clearly different chemical structures as illustrated below arise.

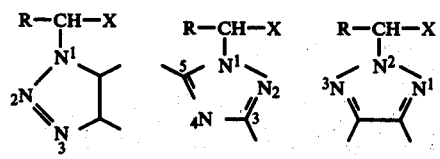

(R and X are as described above.)

Typical examples of the compounds represented by the general formula (I) are illustrated below, but the present invention should not be construed as being limited to these compounds.

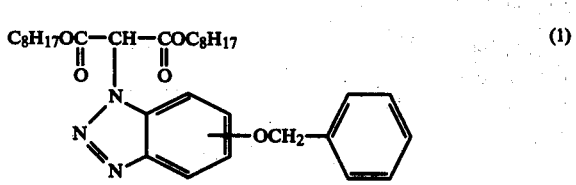

(1)

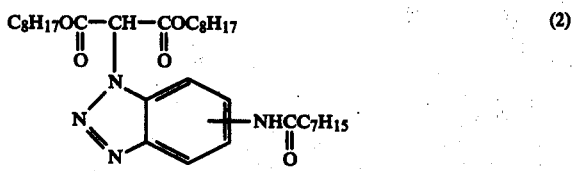

(2)

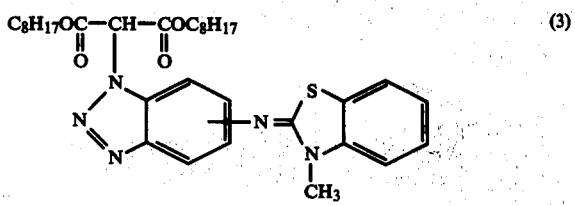

(3)

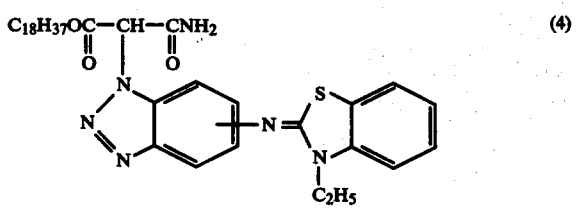

(4)

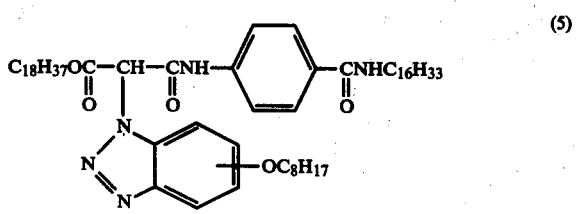

(5)

-continued
(6) 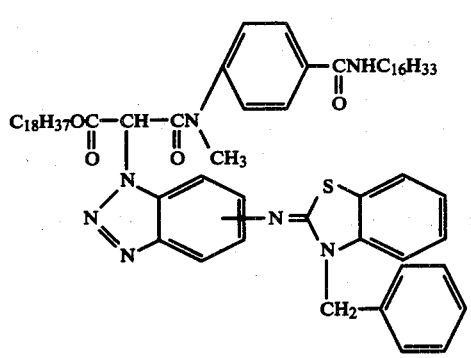
(7) 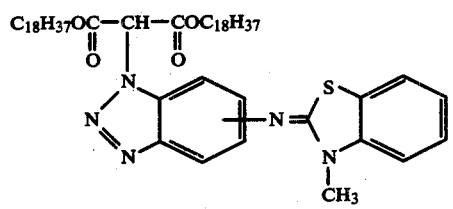
(8) 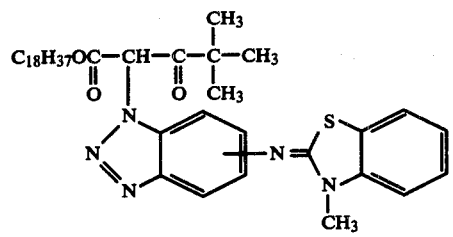
(9) 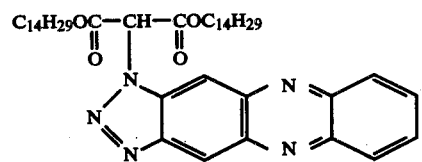
(10) 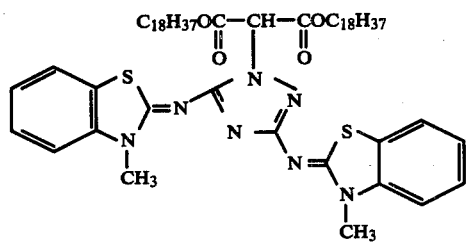
(11) 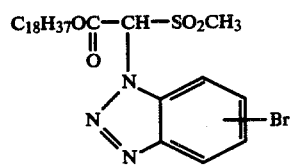
(12) 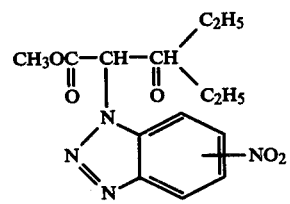
-continued
(13) 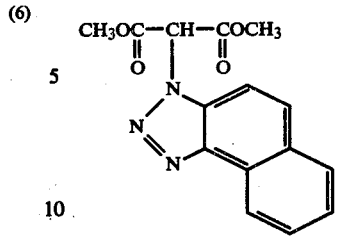
(14) 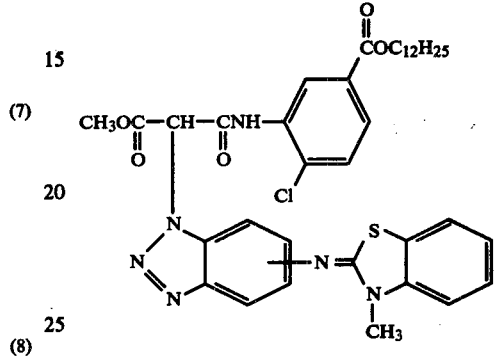
(15) 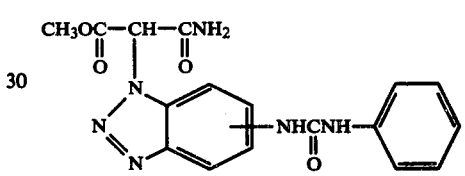
(16) 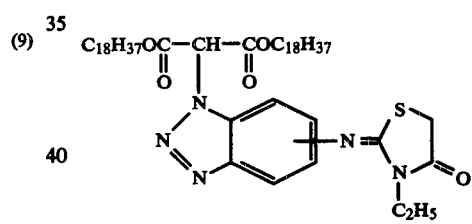
(17) 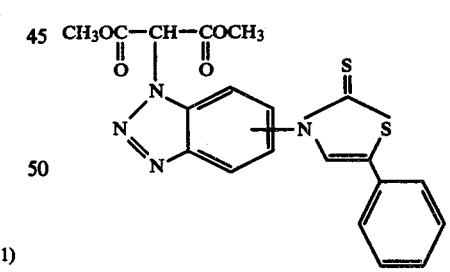
(18) 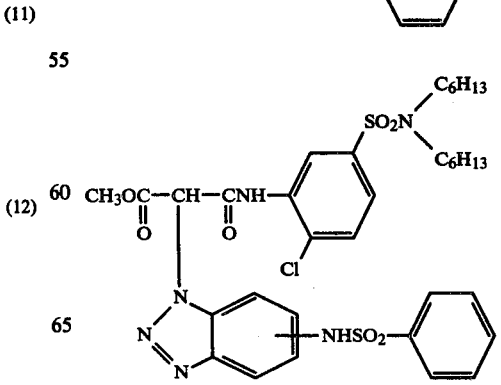

-continued

(19) 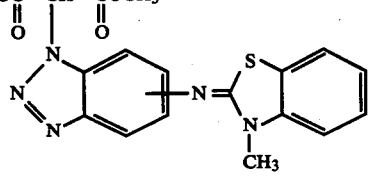

(20) 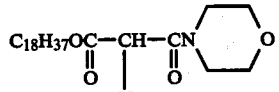

(21) 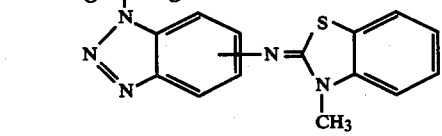

(22) 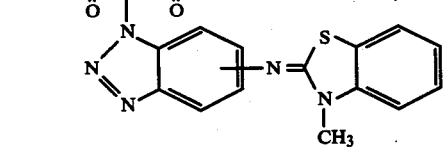

(23) 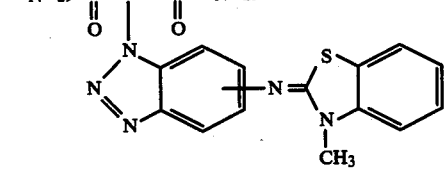

(24) 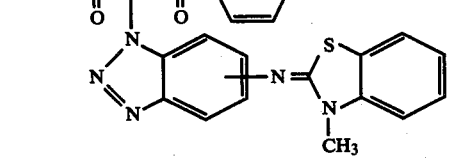

(25) 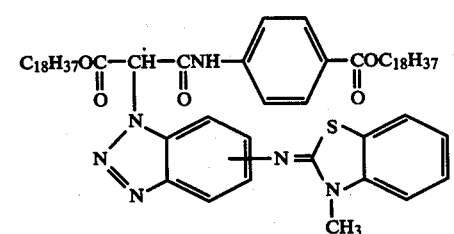
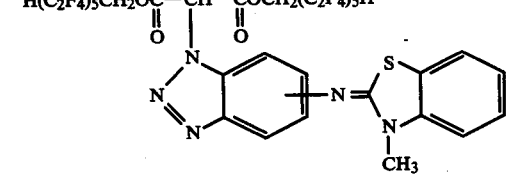

The compounds represented by the general formula (I) can be prepared in the following manner. That is, the active methylene group of a compound having the formula

R—CH₂—X wherein R and X have the same meaning as those in the formula (I), is brominated using conventional techniques, e.g., as disclosed in *Org. Synth. Coll.*, Vol. I, page 245, and then the product is reacted with a compound of the formula

YH wherein Y has the same meaning as in formula (I) above, in the presence of a base in a conventional manner, e.g., as disclosed in British Pat. No. 1,421,123.

Typical methods for preparation of the compounds represented by the general formula (I) are illustrated below. Other compounds can also be prepared in a manner similar to these methods. Unless otherwise indicated herein, all parts, percents, ratios and the like are by weight.

SYNTHESIS EXAMPLE 1

Preparation of

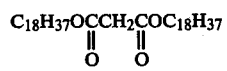

A mixture of 160 g (1 mol) of diethylmalonate, 541 g (2 mols) of octadecyl alcohol and 10 ml of tetrabutoxytitanium was heated at 90° C. for about 4 hours with stirring while removing the ethanol produced under reduced pressure (23 to 27 mmHg) using an aspirator. Then, the product was dissolved in a mixture of 1.0 l of isopropyl alcohol and 0.5 l of methanol. The mixture was stirred for about 5 hours at room temperature to form crystals. Yield: 492 g (81%), M.P.: 58° to 60° C.

Preparation of

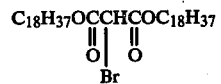

A mixture of 469 g (0.77 mol) of dioctadecylmalonate and methylene chloride was refluxed and 132.8 g (0.83 mol) of bromine was added dropwise thereto over a 50 minute period. Then, the reaction mixture was immediately poured into 2 l of ice-water. The methylene chloride layer was washed three times with water (300 ml). Methylene chloride was removed under reduced pressure and the residue obtained was crystallized from 700 ml of ethyl acetate and 900 ml of acetonitrile to yield 485 g (91.6%). M.P.: 48° to 49° C.

Preparation of Compound (7)

2.2 g (0.04 mol) of potassium hydroxide was dissolved in 20 ml of methanol. 11.2 g (0.04 mol) of 5-(3-methyl-2-benzothiazolinyliden)aminobenzotriazole, which can be prepared, e.g., by the method disclosed in German Patent Application No. (OLS) 2,617,345, was dissolved in 200 ml of dimethylformamide. The methanol solution was mixed with the dimethylformamide solution and then 200 ml of chloroform containing 13.7 g (0.02 mol) of dioctadecyloxy-α-bromomalonate, prepared as described above, dissolved therein was added dropwise thereto over an about one hour period at room temperature (about 20°–30° C.) with stirring. After stirring for one additional hour, the reaction mixture was added to 500 ml of water and 20 ml of concentrated hydrochloric acid (12 N) and stirred. The chloroform layer was washed three times with water (300 ml) and dried with anhydrous sodium sulfate. The solvent was removed under reduced pressure, the residual oily product obtained was dissolved in 100 ml of acetonitrile by heating (70° C.) and allowed to stand at room temperature to form crystals. The crystals were recrystallized from acetonitrile to yield 16.2 g (91.2%). M.P.: 63° to 73° C.

SYNTHESIS EXAMPLE 2

Preparation of Compound (14)

170 g (0.5 mol) of 2-chloro-5-dodecyloxycarbonylaniline and 61.0 g (0.5 mol) of dimethylmalonate were heated at 170° C. for about 5 hours with stirring in an one-liter, three-necked flask while removing methanol produced. The temperature of the reaction mixture was cooled to room temperature to deposit a solid which was recrystallized from ethanol to yield 165 g (75.0%) of α-methoxycarbonyl-2-chloro-5-dedecyloxycarbonylacetanilide.

55.0 g (0.125 mol) of α-methoxycarbonyl-2-chloro-5-dodecyloxycarbonylacetanilide thus prepared was dissolved in one liter of acetic acid and then 20 g (0.125 mol) of bromine dissolved in 100 ml of acetic acid was added dropwise thereto over about a half hour period with stirring. The reaction solution was poured into 2 liters of ice-water and the solid deposited was collected by filtration to obtain 61.8 g (95.2%) of α-bromo-α-methoxycarbonyl-2-chloro-5-dodecyloxycarbonylacetanilide.

13.0 g (0.025 mol) of α-bromo-α-methoxycarbonyl-2-chloro-5-dodecyloxycarbonylacetanilide thua prepared and 10.7 g (0.038 mol) of 5-(3-methyl-2-benzothiazolinyliden)aminobenzotriazole were dissolved in 400 ml of dimethylformamide and to the solution 5.0 g (0.05 mol) of triethylamine was added dropwise at room temperature with stirring. After stirring the reaction mixture for about 5 hours, one liter of water and 200 ml of chloroform were added to the reaction mixture and with stirring 20 ml of concentrated hydrochloric acid (12 N) was added thereto. The solid deposited was removed by filtration and the filtrate was washed with a 2 N hydrochloric acid aqueous solution and then washed twice with water (300 ml) and dried with anhydrous sodium sulfate. The solvent was removed under reduced pressure to obtain 12.6 g (70.3%) of the desired product.

The DIR coupler of the present invention can be used by incorporating it either into a photographic emulsion layer or into a developer solution. In order to render the DIR coupler of the present invention diffusion resistant in a photographic emulsion layer, any known ballast group can be introduced into the coupler molecule. Examples of ballast groups are described in many patent specifications, such as U.S. Pat. No. 2,920,961, Japanese Patent Applications Nos. (OPI) 123,034/1974 and 19,435/1975, etc.

The DIR coupler used in the present invention can be introduced into a photographic layer using any known dispersing method. The DIR coupler of the present invention can be used individually or as a combination of two or more couplers. Further, the DIR coupler of the present invention can be incorporated either into a photographic emulsion layer as a dispersion containing another coupler(s) together therewith or into a photographic subsidiary layer such as an intermediate layer as a dispersion thereof.

The DIR coupler of the present invention is used in a ratio of 0.01 to 100 mol%, preferably 0.1 to 30 mol%, to the coupler(s) other than the DIR coupler in each light-sensitive layer, such as a yellow coupler in a blue-sensitive layer, a magenta coupler in a green-sensitive layer or a cyan coupler in a red-sensitive layer of a color light-sensitive material.

Examples of dye forming couplers which can be used together with the photographic coupler of the present invention are described in the following. The dye forming coupler can be either a four-equivalent coupler or a two-equivalent coupler. Also, a dye forming coupler can be a colored coupler for color correction or a DIR coupler other than that of the present invention.

A known open-chain ketomethylene type coupler can be used as a yellow color coupler. Of these couplers a benzoylacetanilide type compound and a pivaloylacetanilide type compound are advantageous. Specific examples of yellow color couplers usable are described in U.S. Pat. Nos. 2,875,057, 3,265,506, 3,341,331, 3,369,895, 3,408,194, 3,551,155, 3,582,322 and 3,725,072, German Patent Publication No. 1,547,868, German Patent Applications Nos. (OLS) 2,057,941, 2,162,899, 2,213,461, 2,219,917, 2,261,361 and 2,263,875, etc.

A pyrazolone type compound, an indazolone type compound, a cyanoacetyl type compound and the like can be used as a magenta color coupler. Of these couplers a pyrazolone type compound is particularly advantageous. Specific examples of magenta color couplers usable are described in U.S. Pat. Nos. 2,439,098, 2,600,788, 2,983,608, 3,311,476, 3,419,391, 3,519,429, 3,558,319, 3,582,322 and 3,615,506, British Pat. No. 956,261, German Pat. No. 1,810,464, German Patent Application Nos. (OLS) 2,408,665, 2,418,959 and 2,424,467, Japanese Patent Publication No. 2,016/1969, etc.

A phenol derivative, a naphthol derivative, and the like can be used as a cyan color coupler. Specific examples of cyan color couplers are described in U.S. Pat. Nos. 2,369,924, 2,434,272, 2,474,293, 2,600,788, 2,698,794, 2,706,684, 2,896,826, 3,034,892, 3,214,437, 3,253,924, 3,311,476, 3,386,830, 3,458,315, 3,560,212, 3,582,322, 3,583,971 and 3,591,383, German Patent Application Nos. (OLS) 2,163,811 and 2,414,006, Japanese Patent Publication Nos. 6,031/1965 and 28,836/1970, etc.

The compounds described, for example, in Japanese Patent Publication No. 2,016/1969, U.S. Pat. Nos. 2,434,272, 3,476,560 and 3,476,564, German Patent Application No. (OLS) 2,418,959 (as magenta color forming colored couplers), Japanese Patent Publication Nos. 22,335/1963, 20,591/1966, 11,304/1967 and 32,461/1969, U.S. Pat. Nos. 3,034,892 and 3,386,830 (as cyan color forming colored couplers) can be used as a colored coupler.

The compounds described, for example, in U.S. Pat. Nos. 3,148,062, 3,214,437, 3,227,554, 3,253,924, 3,617,291, 3,622,328, 3,639,417, 3,701,783, 3,705,201, 3,770,436 and 3,790,384, Japanese Patent Publication No. 28,836/1970, German Patent Application Nos. (OLS) 2,414,006 and 2,417,914, etc., can be used as a DIR coupler other than that of the present invention.

Also, two or more of the above-described dye-forming couplers, the DIR coupler of this invention and the like can be incorporated in the same layer or the same compound can be incorporated in two or more layers in order to achieve the characteristics required in a light-sensitive material.

Known methods, for example, the method described in U.S. Pat. No. 2,322,027, can be used to incorporate couplers into an emulsion layer. That is, the coupler is dissolved in an organic solvent having a boiling point higher than about 180° C., for example, an alkyl ester of phthalic acid (such as dibutyl phthalate, dioctyl phthalate, etc.), an ester of trimellitic acid (such as tri-tert-octyl trimelitate, etc.), an ester of phosphoric acid (such as diphenyl phosphate, triphenyl phosphate, tricresyl phosphate, dioctyl butyl phosphate, etc.), an ester of citric acid (such as tributyl acetyl citrate, etc.), an alkylamide (such as N,N-diethyl laurylamide, etc.), and the like, or in an organic solvent having a boiling point of about 30° to about 150° C., for example, a lower alkyl acetate (such as ethyl acetate, butyl acetate, etc.), ethyl propionate, secondary butyl alcohol, methyl isobutyl ketone, $\beta$-ethoxyethyl acetate, methyl Cellosolve acetate, and the like, and then the solution is dispersed in a hydrophilic colloid. A mixture of the high boiling organic solvent and the low boiling organic solvent described above can be used, if desired.

A coupler having an acid group such as a carboxylic acid or a sulfonic acid group can be incorporated in a hydrophilic colloid as an aqueous alkaline solution thereof.

These conventional dye forming couplers are generally used in a range from about $2\times10^{-3}$ to about $5\times10^{-1}$ mol, preferably from $1\times10^{-2}$ to $5\times10^{-1}$ mol, per mol of silver in the emulsion layer.

When an imagewise exposed color light-sensitive material is processed in the presence of the DIR coupler of the present invention, the color processing essentially comprises a color development, a bleaching and a fixing step. Each step can be carried out individually. Two or more of these steps may be carried out in a single step by using a processing solution with two or more functions, such as a monobath bleach-fixing solution. Each of the processing steps can be divided into two or more sub-steps, if desired, and it is also possible to employ a combination of processings that comprises a color development, a first fixing and a bleach-fixing. In addition to the above-described steps, the color processing can comprise steps such as pre-hardening, neutralizing, first development (black-and-white development), stabilizing and washing, depending on the need. The processing temperature can be varied depending on the kind of light-sensitive material to be processed or the type of processing. Processing can be carried out at a temperature below about 18° C., but in most cases it is conducted at a temperature above about 18° C., particularly 20° to 60° C. Recently, processings have often been carried out at a temperature of from about 30° to about 60° C. The processing steps can be conducted at the same temperature or at different temperatures.

A color developer solution is an aqueous alkaline solution containing a developing agent and having a pH greater than about 8, preferably between 9 and 12. The developing agent is a compound which has a primary amino group on an aromatic ring and which is capable of developing exposed silver halide or a precursor of such a compound. Preferred examples of developing agents are, for example, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 4-amino-3-methyl-N-ethyl-N-$\beta$-methanesulfonamidoethylaniline, 4-amino-N,N-dimethylaniline, 4-amino-3-methoxy-N,N-diethylaniline, 4-amino-3-methyl-N-ethyl-N-$\beta$-methoxyethylaniline, 4-amino-3-methoxy-N-ethyl-N-$\beta$-methoxyethylaniline, 4-amino-3-$\beta$-methanesulfonamidoethyl-N,N-diethylaniline, and the salts thereof (for example, sulfates, hydrochlorides, sulfites, p-toluenesulfonates, etc.). Other examples of developing agents are described, for example, in U.S. Pat. Nos. 2,193,015 and 2,592,364, Japanese Patent Application No. (OPI) 64,933/1973, and L. F. A. Mason, *Photographic Processing Chemistry*, pp. 226–229, Focal Press, London (1966). The above-described compounds can be used together with 3-pyrazolidones, if desired.

If desired, various additives can be added to the color developer solution. Examples of such additives include alkaline agents (e.g., hydroxides, carbonates and phosphates of alkali metals or ammonia), pH adjusting agents or buffers (e.g., weak acids or bases, such as acetic acid and boric acid, or the salts thereof), development promoters (e.g., compounds described in U.S. Pat. Nos. 2,648,604, 3,671,247, 2,533,990, 2,577,127 and 2,950,970, British Pat. Nos. 1,020,033 and 1,020,032, U.S. Pat. No. 3,068,097, etc.), anti-fogging agents (e.g., alkali metal bromides and alkali metal iodides, nitrobenzimidazoles, such as those described in U.S. Pat. Nos. 2,496,940 and 2,656,271, mercaptobenzimidazole, 5-methylbenzotriazole, 1-phenyl-5-mercaptotetrazole, the anti-fogging agents described in U.S. Pat. Nos. 3,113,864, 3,342,596, 3,295,976, 3,615,522 and 3,597,199, British Pat. No. 972,211, Japanese Patent Publication No. 41,675/1971, and *Kagaku Shashin Binran (Handbook of Scientific Photography)*, Vol. II, pp. 29 to 47, Maruzen, Tokyo (1960), stain or sludge preventing agents (e.g., those described in U.S. Pat. Nos. 3,161,513 and 3,161,514, British Pat. Nos. 1,030,442, 1,144,481 and 1,251,558), and preservatives (e.g., sulfites, bisulfites, hydroxylamine hydrochloride, formsulfites, alkanolamine-sulfite adducts, and the like).

In the course of color processing, an intensification processing can be conducted, as described in German Patent Application No. (OLS) 2,226,770, U.S. Pat. No. 3,826,652, etc.

In the case of a black-and-white development, any of the known developing agents or combinations thereof can be used. The processing solution used can contain almost the same additives as those used in color processing solutions.

The amount of the DIR coupler of the present invention used varies depending on the type of light-sensitive material and processing, but ordinarily the DIR coupler of this invention can be incorporated with advantage into a light-sensitive material in an amount of about 0.00001 mol to about 0.5 mol per mol of the silver halide contained therein, and can be added to a developer solution at a concentration of about $1\times10^{-4}$ to about $1\times10^{-1}$ mol per 1,000 ml of the developer solution.

The silver halide photographic emulsions used in the present invention are those in which light-sensitive silver halides such as silver chloride, silver bromide, silver chlorobromide, silver chloroiodide, silver iodobromide and silver chloroiodobromide are dispersed in a hydrophilic high molecular weight material (protective colloid), such as gelatin, etc., and can be prepared by various methods.

Various conventional additives for ordinary silver halide photographic emulsions such as chemical sensitizers, stabilizers, anti-fogging agents, hardeners, spectral sensitizers, surface active agents, etc., can be incorporated in the silver halide photographic emulsion used in this invention. The photographic emulsions can be coated on an appropriate photographic support using known methods.

The DIR coupler of the present invention can be used in various kinds of silver halide photographic light-sensitive materials. For example, the DIR coupler of this invention can be employed in silver halide photographic light-sensitive materials used for various purposes such as conventional black-and-white light-sensitive materials, lithographic black-and-white light-sensitive materials, light-sensitive materials for X-ray or electron beam recording, black-and-white light-sensitive materials having high resolving power, conventional color light-sensitive materials, color light-sensitive materials for X-ray recording, light-sensitive materials for the color diffusion transfer process, and the like.

According to one embodiment of the present invention, a multilayer color light-sensitive material can comprise a support having thereon a blue-sensitive emulsion layer unit comprising at least one silver halide emulsion layer which is mainly sensitive to blue light (wavelength region of about 500 nm or below) and contains a yellow color coupler capable of forming a yellow dye upon coupling with an oxidation product of an aromatic primary amine developing agent, a green-sensitive emulsion layer unit comprising at least one silver halide emulsion layer which is mainly sensitive to green light (wavelength region of about 500 to about 600 nm) and contains a magenta color coupler capable of forming a magenta dye upon coupling with an oxidation product of an aromatic primary amine developing agent and a red-sensitive emulsion layer unit comprising at least one silver halide emulsion layer which is sensitive to red light (wavelength region of about 500 nm or more) and contains a cyan color coupler capable of forming a cyan dye upon coupling with an oxidation product of an aromatic primary amine developing agent, and optionally photographic subsidiary layers such as an intermediate layer(s) and the DIR coupler of the present invention can be incorporated into at least one of the above-described emulsion layers or intermediate layers.

In the above-described embodiment, each emulsion layer which comprises the blue-sensitive emulsion layer unit, the green-sensitive emulsion layer unit and red-sensitive emulsion layer unit can be positioned in various orders on the support depending on the purpose of use of the light-sensitive material. For example, when each emulsion layer unit comprises a single emulsion layer, a red-sensitive emulsion layer, a green-sensitive emulsion layer and a blue-sensitive emulsion layer are positioned in this order from the support or these layers can be interchanged into another order. Also, when an emulsion layer unit comprises two or more emulsion layers, these emulsion layers are positioned either contiguous to each other or separated by an emulsion layer of another emulsion layer unit.

A useful multilayer color light-sensitive material can also comprise a support having thereon a red-sensitive silver halide photographic emulsion layer unit containing a diffusion resistant uncolored cyan coupler and a diffusion resistant colored cyan coupler, both of which can provide a cyan image upon color development, a green-sensitive silver halide photographic emulsion layer unit containing a diffusion resistant uncolored magenta coupler and a diffusion resistant colored magenta coupler both of which can provide a magenta image upon color development, and a blue-sensitive silver halide photographic emulsion layer unit containing a diffusion resistant uncolored yellow coupler, which can provide a yellow image upon color development, and the DIR coupler of the present invention can be incorporated into at least one layer of the red-sensitive emulsion layer unit, the green-sensitive emulsion layer unit, the blue-sensitive emulsion layer unit or an intermediate layer present therebetween.

The DIR coupler of the present invention has such a high activity that it rapidly reacts with the oxidation product of a color developing agent to release a development inhibitor, so that even a small amount thereof exhibits excellent development inhibiting effects which result in a control of the image tone, a reduced graininess of the image, an improved sharpness of the image and an improved color reproducibility. Further, since the DIR coupler of the present invention is stable when incorporated in a light-sensitive emulsion layer and does not adversely affect the stability of the light-sensitive material, it can be used without concern. Furthermore, the DIR coupler of the present invention can be prepared very easily as described in the Synthesis Examples hereinbefore.

The present invention will be further illustrated in greater detail by reference to the following examples, but the present invention should not be construed as being limited to the following examples.

EXAMPLE 1

Samples of silver halide photographic light-sensitive materials were prepared in accordance with the following Sample 101

On a transparent cellulose triacetate film support were coated the following First Layer to Fourth Layer in this order and dried to prepare the sample. The compositions and methods for preparation of the coating solutions used for each of the layers was as follows.

First Layer: Red-Sensitive Silver Halide Emulsion Layer 1 kg of a high speed silver iodobromide emulsion (silver content: 0.6 mol, iodide content: 6 mol%) was spectrally sensitized using $4 \times 10^{-5}$ mol of Sensitizing Dye I and $1 \times 10^{-5}$ mol of Sensitizing Dye II per mol of silver, respectively. 550 g of Dispersion I prepared by dissolving 100 g of Coupler A into 100 cc of tricresyl phosphate and 200 cc of ethyl acetate, and then dispersing the resulting solution into 1 kg of a 10% gelatin aqueous solution using 4 g of sodium nonylbenzenesulfonate (surface active agent) was added to the spectrally sensitized silver iodobromide emulsion and the mixture was stirred. To the mixture an aqueous solution of 2 g of sodium 2,4-dichloro-6-hydroxytriazine was added as a hardener. The thus-prepared coating solution was coated on a transparent cellulose triacetate film support at a silver coated amount of 2.0 g/m².

Second Layer: Intermediate Layer 50 g of 2,5-di-tert-octylhydroquinone was dissolved in 100 cc of tricresyl phosphate and dispersed in 1 kg of a 10% gelatin aqueous solution in the same manner as described in Dispersion I. 250 g of the thus-prepared dispersion and an aqueous solution of 2 g of sodium 2,4-dichloro-6-hydroxytriazine were added to 1 kg of a 10% gelatin aqueous solution and the mixture was stirred. The coating solution was coated at a dry thickness of 1.5 microns.

Third Layer: Green-Sensitive Silver Halide Emulsion Layer 1 kg of a high speed silver iodobromide emulsion (same as described for the First Layer) was spectrally sensitized using $3 \times 10^{-5}$ mol of Sensitizing Dye III and $1 \times 10^{-5}$ mol of Sensitizing Dye IV per mol of silver, respectively. Using 100 g of Coupler B, Dispersion II was prepared in the same manner as described for Dispersion I. 700 g of Dispersion II was added to the spectrally sensitized silver iodobromide emulsion and an aqueous solution of 2 g of sodium 2,4-dichloro-6-hydroxytriazine was added thereto with stirring. The coating solution was coated at a silver coated amount of 1.5 g/m².

Fourth Layer: Protective Layer

To 1 kg of a 10% gelatin aqueous solution was added 2 g of sodium 2,4-dichloro-6-hydroxytriazine. The solution was coated at a dry thickness of 1.5 microns.

Samples 102 to 106

Samples 102 to 106 were prepared in the same manner as Sample 101 except that the optimum amount of DIR coupler (as shown in Table 1 below) was additionally incorporated into the coupler solvent in Dispersion I used in Sample 101.

The compounds used for the preparation of the above-described samples were:

Sensitizing Dye I: Pyridinium salt of anhydro-5,5'-dichloro-3,3'-disulfopropyl-9-ethylthiacarbocyanine hydroxide Sensitizing Dye II: Triethylamine salt of anhydro-9-ethyl-3,3'-di(3-sulfopropyl)-4,5,4',5'-dibenzothiacarbocyanine hydroxide Sensitizing Dye III: Sodium salt of anhydro-9-ethyl-5,5'-dichloro-3,3'-disulfopropyloxacarbocyanine Sensitizing Dye IV: Sodium salt of anhydro-5,6,5',6'-tetrachloro-1,1'-diethyl-3,3'-disulfopropoxyethoxyethylimidazolocarbocyanine hydroxide Coupler A: 1-Hydroxy-N-[γ-(2,4-di-tert-amylphenoxy)propyl]-2-naphthamide Coupler B: 1-(2,4,6-Trichlorophenyl)-3-[3-(2,4-di-tert-amylphenoxyacetamido)benzamido]-5-pyrazolone (4-equivalent coupler)

Comparison DIR Coupler (D-1): α-(1-Phenyl-5-tetrazolylthio)octylmalonate

Comparison DIR Coupler (D-2): 4-n-Stearyloxy-ω-(5- or 6-octanamidobenzotriazol-1-yl)acetophenone Samples 101 to 106 were exposed (20 CMS; 1/100 sec.) stepwise using red light and then exposed uniformly (20 CMS; 1/100 sec.) using green light, and subjected to the following processing steps at 38° C.

| 1. Color Development | 3 min and 15 sec |
| 2. Bleaching | 6 min and 30 sec |
| 3. Washing | 3 min and 15 sec |
| 4. Fixing | 6 min and 30 sec |
| 5. Washing | 3 min and 15 sec |
| 6. Stabilizing | 3 min and 15 sec |

In addition, these samples were line image exposed (sufficient to produce a maximum density in the red-sensitive layer of 1.5) to soft X-rays through a slit with a 4 mm width and a slit with a 10 μm width and subjected to the same processing as above.

The processing solutions used in the above steps had the following compositions.

| Color Developer Solution | |
|---|---|
| Sodium Nitrilotriacetate | 1.0 g |
| Sodium Sulfite | 4.0 g |
| Sodium Carbonate | 30.0 g |
| Potassium Bromide | 1.4 g |
| Hydroxylamine Sulfate | 2.4 g |
| 4-(N-Ethyl-N-β-hydroxethylamino)-2-methylaniline Sulfate | 4.5 g |
| Water to make | 1 l |

| Bleaching Solution | |
|---|---|
| Ammonium Bromide | 160.0 g |
| Ammonia (28% aq. soln.) | 25.0 ml |
| Sodium Ferric Ethylenediaminetetraacetate | 130 g |
| Glacial Acetic Acid | 14 ml |
| Water to make | 1 l |

| Fixing Solution | |
|---|---|
| Sodium Tetrapolyphosphate | 2.0 g |
| Sodium Sulfite | 4.0 g |
| Ammonium Thiosulfate (70% aq. soln.) | 175.0 ml |
| Sodium Bisulfite | 4.6 g |
| Water to make | 1 l |

| Stabilizing Solution | |
|---|---|
| Formaldehyde (38% aq. soln.) | 8.0 ml |
| Water to make | 1 l |

In the characteristic curve thus obtained, when the gradation of the curve of the red filter optical density vs. log (exposure amount) (which corresponds to the First Layer) is designated $\gamma_R$ and the gradation of the curve of the green filter optical density vs. log (exposure amount) (which corresponds to the Third Layer) is designated $\gamma_G$, the value of $\gamma_G/\gamma_R$ is considered to be the amount of interlayer effects from the First Layer to the Third Layer ($\gamma_R$ values of the samples other than Sample 101 are substantially constant). That is, the value of $\gamma_G/\gamma_R$ is minus and larger numerical values mean larger interlayer effects. The $\gamma_G/\gamma_R$ value of each sample is shown in Table 1 below.

The optical density of each sample obtained by line image exposure with soft X-rays was measured by microdensitometer tracing with red light. When the density of the line image with a 10μ width is designated $D_1^R$ and the density of the line image with a 4 mm width is designated $D_2^R$, the value of $(D_1^R-D_2^R)/D_1^R$ means the amount of edge effects of the sample when the sample is observed with red light. The value of $(D_1^R-D_2^R)/D_1^R$ of each sample is shown in Table 1 below.

TABLE 1

| Sample No. | DIR Coupler Compound | Amount (mol%) | Interimage Effects ($\gamma_G/\gamma_R$) | Edge Effects $(D_1^R-D_2^R)/D_1^R$ |
|---|---|---|---|---|
| 101* | — | — | 0.08 | 0.04 |
| 102** | Compound (1) | 17 | −0.35 | 0.23 |
| 103** | Compound (2) | 16 | −0.30 | 0.20 |
| 104** | Compound (3) | 14 | −0.39 | 0.28 |

-continued

| Sample No. | DIR Coupler Compound | Amount (mol%) | Interimage Effects ($\gamma_G/\gamma_R$) | Edge Effects ($D_1^R - D_2^R)/D_1^R$ |
|---|---|---|---|---|
| 105*** | Coupler D-1 | 20 | −0.09 | 0.10 |
| 106*** | Coupler D-2 | 20 | −0.07 | 0.09 |

*Control
**Present Invention
***Comparison

Amount: mol% DIR compound or coupler to Coupler A. The inertia sensitivities of the samples were substantially constant.

From the results shown above it is apparent that Compounds (1), (2) and (3) of the present invention provide remarkably large interlayer effects to the adjacent layer and edge effects in the layer to which the compound of this invention was added in comparison with Comaprison DIR Couplers D-1 and D-2 even though the amount of the compounds of this invention is smaller than that of the comparison couplers. Furthermore, although Compound (1), (2) or (3) was added in an amount of 15 to 20 mol%, no color turbidity of cyan color in the red-sensitive layer due to the compound formed in the coupling reaction was observed. This shows that the compound formed is substantially colorless.

EXAMPLE 2

On a cellulose triacetate film support were coated layers having the compositions set forth below to prepare a multilayer color light-sensitive material. The compounds indicated by an asterisk are the same compounds described in Example 1.

First Layer: Antihalation Layer (AHL)
A gelatin layer (3 m$\mu$) containing black colloidal silver (300 mg/m$^2$)

Second Layer: Intermediate Layer (ML)
A gelatin layer (2 m$\mu$) containing a dispersion of 2,5-di-tert-octylhydroquinone Third Layer: First Red-Sensitive Silver Halide Emulsion Layer (RL$_1$)

| A silver iodobromide emulsion (iodide content: 5 mol%) | |
|---|---|
| silver coated amount: 1.79 g/m$^2$ | |
| Sensitizing Dye I* | 6 × 10$^{-5}$ mol per mol of silver |
| Sensitizing Dye II* | 1.5 × 10−5mol per mol of silver |
| Coupler A* | 0.04 mol per mol of silver |
| Coupler C-1 | 0.0015 mol per mol of silver |
| Coupler C-2 | 0.0015 mol per mol of silver |
| Compound (7) | 0.003 mol per mol of silver |

Fourth Layer: Second Red-Sensitive Silver Halide Emulsion Layer (RL$_2$)

| A silver iodobromide emulsion (iodide content: 4 mol %) | |
|---|---|
| silver coated amount: 1.4 g/m$^2$ | |
| Sensitizing Dye I* | 3 × 10$^{-5}$mol per mol of silver |
| Sensitizing Dye II* | 1.2 × 10$^{-5}$mol per mol of silver |
| Coupler A* | 0.005 mol per mol silver |
| Coupler C-1 | 0.0008 mol per mol of silver |
| Coupler C-2 | 0.0008 mol per mol of silver |
| Coupler C-3 | 0.015 mol per mol of silver |
| Compound (7) | 0.0003 mol per mol of silver |

Fifth Layer: Intermediate Layer (ML)
Same as the Second Layer

Sixth Layer: First Green-Sensitive Silver Halide Emulsion Layer (GL$_1$)

| A silver iodobromide emulsion (iodide content: 4 mol%) | |
|---|---|
| silver coated amount: 1.5 g/m$^2$ | |
| Sensitizing Dye III* | 3 × 10$^{-5}$mol per mol of silver |
| Sensitizing Dye IV* | 1 × 10$^{-5}$mol per mol of silver |
| Coupler B* | 0.05 mol per mol of silver |
| Coupler M-1 | 0.008 mol per mol of silver |
| Compound (7) | 0.005 mol per mol of silver |

Seventh Layer: Second Green-Sensitive Silver Halide Emulsion Layer (GL$_2$)

| A silver iodobromide emulsion (iodide content: 5 mol%) | |
|---|---|
| silver coated amount: 1.6 g/m$^2$ | |
| Sensitizing Dye III* | 2.5 × 10$^{-5}$mol per mol of silver |
| Sensitizing Dye IV* | 0.8 × 10$^{-5}$mol per mol of silver |
| Coupler B* | 0.02 mol per mol of silver |
| Coupler M-1 | 0.003 mol per mol of silver |
| Compound (7) | 0.001 mol per mol of silver |

Eighth Layer: Yellow Filter Layer (YEL)
A gelatin layer (3 m$\mu$) containing yellow colloidal silver (300 mg/m$^2$) and a dispersion of 2,5-di-tert-octylhydroquinone Ninth Layer: First Blue-Sensitive Silver Halide Emulsion Layer (BL$_1$)

| A silver iodobromide emulsion (iodide content: 6 mol%) | |
|---|---|
| silver coated amount: 1.5 g/m$^2$ | |
| Coupler Y-1 | 0.25 mol per mol of silver |
| Compound (7) | 0.003 mol per mol of silver |

Tenth Layer: Second Blue-Sensitive Silver Halide Emulsion Layer (BL$_2$)

| A silver iodobromide emulsion (iodide content: 6 mol%) | |
|---|---|
| silver coated amount: 1.1 g/m$^2$ | |
| Coupler Y-1 | 0.06 mol per mol of silver |

Eleventh Layer: Protective Layer (PL)
A gelatin layer containing an ultra-fine grain silver iodobromide emulsion (containing 0.06 mol of silver per kg of emulsion, having an iodide content of 1.4 mol%, and having an average grain size of 0.03$\mu$), and polymethyl methacrylate particles (having a diameter of about 1.5$\mu$)
silver coated amount: 2.3 g/m$^2$ A gelatin hardener and a surface active agent as described in Example 1 were incorporated into each of the layers in addition to the above-described components.

The thus prepared sample was designated Sample 201.

Samples 202 to 204

Samples 202 to 204 were prepared in the same manner as Sample 201 except that Compound (8), Comparison DIR Couplers D-3 and D-4 were used in place of Compound (7) of Sample 201, respectively. The amounts of the DIR couplers used are shown in Table 2.

TABLE 2

| Layer Added | Sample 201 Compound | Amount | Sample 202 Compound | Amount | Sample 203 Compound | Amount | Sample 204 Compound | Amount |
|---|---|---|---|---|---|---|---|---|
| $RL_1$ | (7) | 0.003 | (8) | 0.0045 | D-3 | 0.006 | D-4 | 0.009 |
| $RL_2$ | " | 0.0003 | " | 0.0004 | " | 0.005 | " | 0.0008 |
| $GL_1$ | " | 0.005 | " | 0.0075 | " | 0.008 | " | 0.015 |
| $GL_2$ | " | 0.001 | " | 0.0015 | " | 0.0015 | " | 0.003 |
| $BL_1$ | " | 0.002 | " | 0.004 | " | 0.0025 | " | 0.007 |

Amount: mol per mol of silver

The couplers used for the preparation of these samples were as follows.

Coupler C-1: 1-Hydroxy-4-[2-(2-hexyldecyloxycarbonyl)phenylazo]-2-[N-(1-naphthyl)]naphthamide
Coupler C-2: 1-Hydroxy-4-[4-(ethoxycarbonyl)phenylazo]-2-(N-dodecyl)naphthamide
Coupler C-3: 1-Hydroxy-4-iodo-2-(N-dodecyl)naphthamide
Coupler M-1: 1-(2,4,6-Trichlorophenyl)-3-hexadecanamido-4-(4-hydroxyphenyl)azo-5-pyrazolone
Coupler Y-1: α-(2,4-Dioxo-5,5-dimethyloxazolidinyl)-α-pivaloyl-2-chloro-5-[α-2,4-di-tert-amylphenoxy)-butyramido]acetanilide
Comparison DIR Coupler D-3: m-Dodecyl-sulfonamido-ω-(4-methoxybenzoyloxy)-ω-(1-phenyl-5-tetrazolylthio)acetophenone
Comparison DIR Coupler D-4: p-Tetradecyloxy-ω-(4-methoxyphenoxy)-ω-(1-phenyl-5-tetrazolylthio)acetophenone The samples thus prepared were exposed (20 CMS; 1/100 sec) stepwise with white light and subjected to sensitometry as described in Example 1. The sensitivity and gradation in each emulsion layer of Samples 201 to 204 were approximately equal.

The evaluations of edge effects and interlayer effects of these samples were carried out in the same manner as described in Example 1. The results obtained are shown in Table 3.

Further, each sample which was fully exposed to white light was processed in the same manner as described in Example 1. The residual silver contained in each sample was determined by fluorescent X-ray analysis. The results obtained are shown in Table 3 below.

TABLE 3

| Sample No. | Light Used for Measurement | Edge Effects $(D_1 D_2)/D_1$ | Interimage Effects $\gamma_R/\gamma_G$ | $\gamma_G/\gamma_R$ | Amount of Residual Silver ($\mu g/cm^2$) |
|---|---|---|---|---|---|
| 201* | Blue light | 0.28 | | | |
| | Green light | 0.33 | −0.33 | −0.32 | 0.8 |
| | Red light | 0.41 | | | |
| 202* | Blue light | 0.25 | | | |
| | Green light | 0.31 | −0.30 | −0.25 | 0.4 |
| | Red light | 0.36 | | | |
| 203** | Blue light | 0.10 | | | |
| | Green light | 0.17 | −0.14 | −0.14 | 6.9 |
| | Red light | 0.18 | | | |
| 204** | Blue light | 0.10 | | | |
| | Green light | 0.15 | −0.10 | −0.07 | 10.1 |
| | Red light | 0.13 | | | |

*Invention
**Comparison

It is apparent from the results shown above that Samples 201 and 202 which contain Compounds (7) and (8) of the present invention, respectively, exhibit greater edge effects and interlayer effects as compared with Samples 203 and 204 which contain Comparison Compounds D-3 and D-4, respectively, even though the amount of Compound (7) or (8) was smaller than that of Comparison Compound D-3 and D-4. Further, according to the present invention, the amount of residual silver present is extremely small and thus color turbidity due to insufficient bleaching of silver was prevented.

Furthermore, these samples were cut into films of 35 mm size and photographed to form negative films. Color prints were prepared by printing the negative films thus-obtained using an enlarging technique. The color prints obtained using Samples 201 and 202 had a fine graininess and a sharp image and showed clear colors, particularly clearly reproduced green and red colors in comparison with those obtained using Samples 203 and 204.

These results indicated that Compounds (7) and (8) had excellent characteristics in terms of improved graininess, sharpness and color reproduction.

EXAMPLE 3

Sample 301 having a layer structure as shown in FIG. 1 was prepared as follows. In a red-sensitive silver iodobromide emulsion (AgI: 7 mol%) which was spectrally sensitized using Sensitizing Dyes I and II described in Example 1, 1-hydroxy-4-chloro-2-n-dodecylnaphthamide was emulsified and mixed as a cyan coupler. In a green-sensitive silver iodobromide emulsion (AgI: 6 mol%) which was spectrally sensitized using Sensitizing Dyes III and IV described in Example 1, 1-(2,4,6-trichlorophenyl)-3-[3-(2,4-di-tert-amylphenoxyacetamido)benzamido]-5-pyrazolone was emulsified and mixed as a magenta coupler. In a blue-sensitive silver iodobromide emulsion (AgI: 6 mol%) α-pivaloyl-α-[4-(4-benzyloxysulfonyl)phenoxy]-2-chloro-5-[γ-(2,4-di-tert-amylphenoxy)butyramido]acetanilide was emulsified and mixed as a yellow coupler. These emulsions were coated on a cellulose triacetate film support to prepare a color reversal photographic light-sensitive material Sample 301.

Additionally, in the emulsification of each coupler, dibutyl phthalate and tricresyl phosphate were used as a solvent for the couplers, sorbitan monolaurate and sodium dodecylbenzenesulfonate were used as an emulsifier.

With Sample 301, an antihalation layer (3 mμ) containing black colloidal silver (300 mg/m²) and a gelatin intermediate layer (3 mμ) was provided under the red-sensitive silver halide emulsion layer, a filter layer (3 mμ) of yellow colloidal silver (300 mg/m²) was provided between the green-sensitive silver halide emulsion layer and the blue-sensitive silver halide emulsion layer, an intermediate layer (3 mμ) comprising gelatin containing dispersed therein di-tert-anylhydroquinone was provided between the green-sensitive silver halide emulsion layer and the red-sensitive silver halide emulsion layer, and a protective layer (2 mμ) mainly comprising gelatin was provided on the blue-sensitive silver halide emulsion layer.

The gelatin hardener and the surface active agent were added to each layer the same as in Example 1.

The coated silver amount of the red-sensitive silver halide emulsion layer was 1.5 g/m$^2$, that of the green-sensitive silver halide emulsion layer was 1.5 g/m$^2$, and that of the blue-sensitive silver halide emulsion layer was 0.9 g/m$^2$.

The molar ratios of silver/coupler in each silver halide emulsion layer were 8.0 in the red-sensitive silver halide emulsion layer, 9.5 in the green-sensitive silver halide emulsion layer and 5.0 in the blue-sensitive silver halide emulsion layer.

Samples 302 to 305

Samples 302 to 305 were prepared in the same manner as Sample 301 except that the compounds shown in Table 4 were additionally dissolved in the coupler solvents used for the cyan coupler and the magenta coupler, emulsified, and added to the red-sensitive silver halide emulsion layer and the green-sensitive silver halide emulsion layer, respectively, of Sample 301.

Samples 301 to 305 thus prepared were stepwise exposed (20 CMS; 1/100 sec) to red light and then uniformly exposed (0.5 CMS; 1/100 sec) to green light so as to provide a color density of 70% of the maximum color density obtained by color development of the green-sensitive silver halide emulsion layer and subjected to the color reversal processing as shown by the following.

| Processing Step | Temperature (°C.) | Time (min) |
|---|---|---|
| First Development (black and white) | 30 | 5 |
| Stopping Bath | " | 1 |
| Washing | " | 2 |
| Fogging Bath | " | 2 |
| Color Development | " | 7 |
| Stopping Bath | " | 2 |
| Hardening Bath | " | 2 |
| Washing | " | 2 |
| Bleaching Bath | " | 4 |
| Washing | " | 2 |
| Fixing Bath | " | 4 |
| Washing | " | 2 |
| Drying | " | |

| Composition of the First Developer Solution: | |
|---|---|
| Sodium Sulfite | 60.0 g |
| 1-Phenyl-3-pyrazolidone | 0.3 g |
| Hydroquinone | 5.0 g |
| Sodium Carbonate (monohydrate) | 41.0 g |
| Potassium Bromide | 2.0 g |
| Potassium Iodide (1% aq. soln.) | 1.0 ml |
| Potassium Thiocyanate (1N aq. soln.) | 10.0 ml |
| Sodium Hydroxide (10% aq. soln.) | 2.0 ml |
| Water to make | 1.0 l |

| Composition of Stopping Solution: | |
|---|---|
| Sodium Acetate | 30 g |
| Glacial Acetic Acid | 8 ml |
| Water to make | 1 l |

| Composition of Fogging Bath: | |
|---|---|
| Sodium Hydroxide | 2.0 g |
| Sodium Borohydride | 0.1 g |
| Water to make | 1.0 l |

| Composition of Color Developer Solution: | |
|---|---|
| Benzyl Alcohol | 5.0 ml |
| Sodium Hydroxide | 0.5 g |
| Diethylene Glycol | 3.0 ml |
| Sodium Hexametaphosphate | 2.0 g |
| Sodium Sulfite | 2.0 g |
| Potassium Bromide | 2.0 g |
| 4-Amino-3-methyl-N-ethyl-β-hydroxyethyl-aniline Sesquisulfate (monohydrate) | 5.0 g |
| Citrazinic Acid | 0.4 g |
| Metaboric Acid | 0.5 g |
| Borax | 77.0 g |
| Water to make | 1.0 l |

| Composition of Hardening Bath: | |
|---|---|
| Sodium Hexametaphosphate | 1.0 g |
| Borax (hexahydrate) | 20.0 g |
| Formaldehyde (37% aq. soln.) | 10.0 ml |
| Water to make | 1.0 l |

| Composition of Bleaching Solution: | |
|---|---|
| Iron (III) Sodium Ethylenediamine-tetraacetate (dihydrate) | 30.0 g |
| Potassium Bromide | 50.0 g |
| Disodium Ethylenediaminetetraacetate | 5.0 g |
| Boric Acid | 3.0 g |
| Borax | 1.5 g |
| Water to make | 1.0 l |

| Composition of Fixing Solution: | |
|---|---|
| Sodium Thiosulfate | 150 g |
| Sodium Sulfite | 15 g |
| Borax | 12 g |
| Glacial Acetic Acid | 15 ml |
| Potassium Alum | 20 g |
| Water to make | 1 l |

Figure 2:
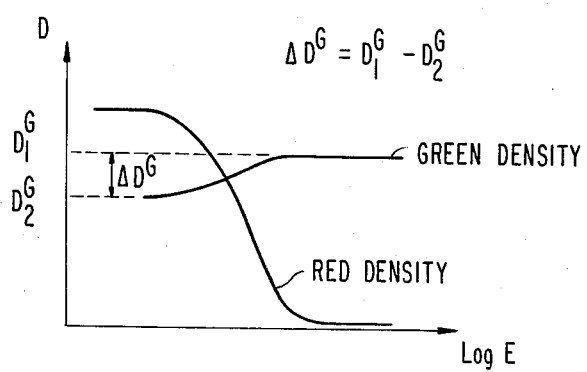

The optical densities of the samples thus-processed were measured and the difference of the green density $\Delta D^G$ was determined as shown in FIG. 2. The results obtained are shown in Table 4. The value of $\Delta D^G$ is plus and larger numerical values mean larger interlayer effects.

As can be clearly understood from the results in Table 4, Samples 302 and 303 containing Compounds (3) and (5) of the present invention respectively show larger interlayer effects in comparison with Samples 304 and 305 containing Comparison DIR Couplers D-1 and D-2.

TABLE 4

| Sample No. | Layer Added | Compound | Amount (mol%) | Interlayer Effects $\Delta D^G$ |
|---|---|---|---|---|
| 301 | GL | — | — | −0.14 |
| | RL | — | | |
| 302 | GL | Compound (3) | 2 | 0.18 |
| | RL | " | 4 | |
| 303 | GL | Compound (5) | 3 | 0.17 |

TABLE 4-continued

| Sample No. | Compound Layer Added | Compound | Amount (mol%) | Interlayer Effects $\Delta D^G$ |
|---|---|---|---|---|
| | RL | " | 6 | |
| 304 | GL | Comparison DIR Coupler D-1 | 6 | 0.08 |
| | RL | " | 12 | |
| 305 | GL | Comparison DIR Coupler D-2 | 8 | 0.06 |
| | RL | " | 16 | |

Amount: mol% to total coupler amount

While the invention has been described in detail and with reference to specific embodiments thereof, it will be apparent to one skilled in the art that various changes and modifications can be made therein without departing from the spirit and scope thereof.

What is claimed is:

1. A photographic silver halide emulsion containing a coupling compound represented by the following general formula (I):

 (I)

wherein R represents

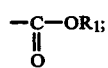

X represents

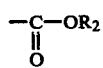

; $R_1$ and $R_2$ each represents an aliphatic group or an aromatic group; and Y represents a group capable of being released from the compound represented by the general formula (I) upon reaction with the oxidation product of a color developing agent to provide a compound which has a development inhibiting effect and having a benzotriazole ring bonded to the carbon atom through the nitrogen atom at the 1-position thereof, said Y being selected from a 5- or 6-benzyloxybenzotriazole-1-yl group, a 5- or 6-octanamidobenzotriazole-1-yl group, a 5- or 6-(3-methylbenzothiazolyliden)aminobenzotriazol-1-yl group, a 5- or 6-(3-ethylbenzothiazolinyliden)aminobenzotriazolyl group or a 5- or 6-(3-benzylbenzothiazolinyliden)aminobenzotriazolyl group.

2. The photographic light-sensitive material as claimed in claim 1, wherein Y represents a benzotriazolyl group substituted with a group represented by the following general formula (IIA):

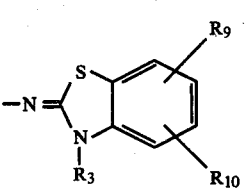 (IIA)

wherein $R_3$ represents an aliphatic group; and $R_9$ and $R_{10}$, which may be the same or different, each represents a hydrogen atom, a halogen atom, an aliphatic group, an alkoxy group, a hydroxy group or an aromatic group.

3. The photographic light-sensitive material as claimed in claim 2, wherein $R_9$ and $R_{10}$, which may be the same or different, each represents a hydrogen atom, a methyl group, an ethyl group, a chlorine atom, a methoxy group, an ethoxy group or a hydroxyl group.

4. The photographic light-sensitive material as claimed in claim 1, wherein said coupling compound represented by the general formula (I) is present in said silver halide emulsion layer in an amount of from about 0.00001 to about 0.5 mol per mol of silver halide in said silver halide emulsion layer.

5. A multilayer color photographic light-sensitive material comprising a support having thereon at least one blue-sensitive silver halide emulsion layer containing a yellow color forming coupler, at least one green-sensitive silver halide emulsion layer containing a magenta color forming coupler and at least one red-sensitive silver halide emulsion layer containing a cyan coupler, with at least one of said silver halide emulsion layers containing a coupling compound represented by the following general formula (I):

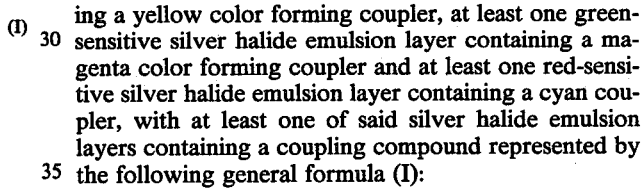 (I)

wherein R represents

X represents

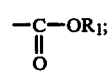

; $R_1$ and $R_2$ each represents an aliphatic group or an aromatic group; and Y represents a group capable of being released from the compound represented by the general formula (I) upon reaction with the oxidation product of a color developing agent to provide a compound which has a development inhibiting effect and having a benzotriazole ring bonded to the carbon atom through the nitrogen atom at the 1-position thereof, said Y being selected from a 5- or 6-benzyloxybenzotriazole-1-yl group, a 5- or 6-octanamidobenzotriazole-1-yl group, a 5- or 6-(3-methylbenzothiazolinyliden)aminobenzotriazol-1-yl group, a 5- or 6-(3-ethylbenzothiazolinyliden)aminobenzotriazolyl group or a 5- or 6-(3-benzylbenzothiazolinyliden)aminobenzotriazolyl group.

6. A photographic light-sensitive material comprising a support having thereon at least one layer of the silver halide emulsion as claimed in claim 1.

7. A photographic color developer solution containing a coupler compound represented by the following general formula (I):

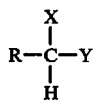

wherein R represents

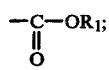

X represents

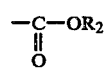

; $R_1$ and $R_2$ each represents an aliphatic group or an aromatic group; and Y represents a group capable of being released from the compound represented by the general formula (I) upon reaction with the oxidation product of a color developing agent to provide a compound which has a development inhibiting effect and a benzotriazole ring bonded to the carbon atom through the nitrogen atom at the 1-position thereof, said Y being selected from a 5- or 5-benzyloxybenzotriazole-1-yl group, a 5- or 6-octanamidobenzotriazole-1-yl group, a 5- or 6-(3-methylbenzothiazolinyliden)aminobenzotriazol-1-yl group, a 5- or 6-(3-ethylbenzothiazolinyliden)aminobenzotriazolyl group or a 5- or 6-(3-benzylbenzothiazolinyliden)aminobenzotriazolyl group.

8. A method of forming a photographic image comprising developing an imagewise exposed photographic light-sensitive material having thereon at least one silver halide emulsion layer in the presence of a coupling compound represented by the following general formula (I):

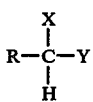

wherein R represents

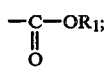

X represents

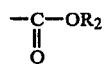

; $R_1$ and $R_2$ each represents an aliphatic group or an aromatic group; and Y represents a group capable of being released from the compound represented by the general formula (I) upon reaction with the oxidation product of a color developing agent to provide a compound which has a development inhibiting effect and a benzotriazole ring bonded to the carbon atom through the nitrogen atom at the 1-position thereof, said Y being selected from a 5- or 6-benzyloxybenzotriazole-1-yl group, a 5- or 6-octanamidobenzotriazole-1-yl group, a 5- or 6-(3-methylbenzothiazolinyliden)aminobenzotriazol-1-yl group, a 5- or 6-(3-ethylbenzothiazolinyliden)aminobenzotriazolyl group or a 5- or 6-(3-benzylbenzothiazolinyliden)aminobenzotriazolyl group.

9. The photographic silver halide emulsion of claim 1, wherein said coupling compound yields, upon reaction with the oxidation product of a color developing agent, a color which does not substantially contribute to a resulting finished color image.

10. A multi-layer color photographic light-sensitive material as claimed in claim 5, wherein said coupling compound yields, upon reaction with the oxidation product of a color developing agent, a color which does not substantially contribute to a resulting finished color image.

11. A photographic color developer solution as claimed in claim 7, wherein said coupling compound yields, upon reaction with the oxidation product of a color developing agent, a color which does not substantially contribute to a resulting finished color image.

12. A method as claimed in claim 8, wherein said coupling compound yields, upon reaction with the oxidation product of a color developing agent, a color which does not substantially contribute to a resulting finished color image.

13. The photographic light-sensitive material as claimed in claim 1, wherein said coupling compound is

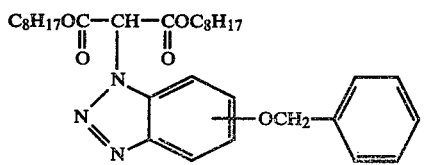

14. The photographic light-sensitive material as claimed in claim 1, wherein said coupling compound is

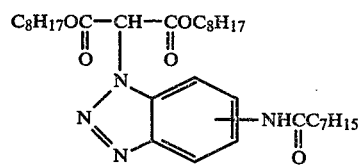

15. The photographic light-sensitive material as claimed in claim 1, wherein said coupling compound is

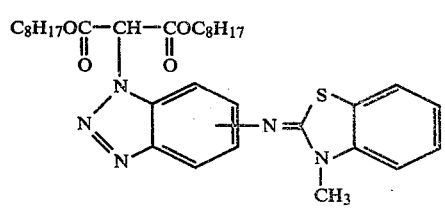

16. The photographic light-sensitive material as claimed in claim 1, wherein said coupling compound is
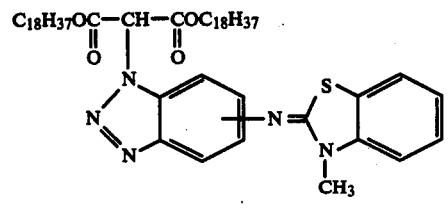
* * * * *